United States Patent [19]
Sentilles

[11] Patent Number: 5,871,522
[45] Date of Patent: Feb. 16, 1999

[54] APPARATUS AND METHOD FOR PROJECTING GERMICIDAL ULTRAVIOLET RADIATION

[75] Inventor: J. Bruce Sentilles, Charlotte, N.C.

[73] Assignee: Senasco, Inc., Charlotte, N.C.

[21] Appl. No.: 739,030

[22] Filed: Oct. 28, 1996

[51] Int. Cl.$^6$ .................................................... A61N 5/06
[52] U.S. Cl. ............................................ 607/94; 607/88
[58] Field of Search ................. 607/88, 94; 250/455.11, 250/454.11

[56] References Cited

U.S. PATENT DOCUMENTS

| | | |
|---|---|---|
| 2,274,298 | 2/1942 | Koch et al. . |
| 3,107,863 | 10/1963 | Potapenko . |
| 4,298,005 | 11/1981 | Mutzhas . |
| 4,444,190 | 4/1984 | Mutzhas . |
| 4,558,700 | 12/1985 | Mutzhas . |
| 4,625,120 | 11/1986 | Capari . |
| 4,839,513 | 6/1989 | Wijtsma . |
| 4,909,254 | 3/1990 | Wilkinson . |
| 5,344,433 | 9/1994 | Talmore ..................................... 607/88 |

OTHER PUBLICATIONS

Commercial Lighting Design, Inc., "Ultraviolet Supplemental Air Disinfection", 8 pages (undated).

J. D. Lowell, M.D. and R. B. Kundsin, Ph.D., "Ultraviolet Radiation: Its Beneficial Effect on the Operating Room Environment and the Incidence of Deep Wound Infection Following Total Hip and Total Knee Arthroplasty", pp. 2–10 (undated).

Commerical Lighting Design, Inc., "Understanding and Applying Ultraviolet Germicidal Irradiation" Mar. 1994, pp. 1–7.

Dexter Industrial Green, "Preliminary Manual IL400 Radiometer" pp. 40–41 (undated).

*Primary Examiner*—Jeffrey R. Jastrzab
*Assistant Examiner*—Ryan Carter
*Attorney, Agent, or Firm*—Kennedy Covington Lobcell & Hickman, LLP

[57] ABSTRACT

An apparatus and method for projecting a concentrated beam of germicidal ultraviolet radiation onto a preselected target area on the body of a patient undergoing surgery, without substantial emanation of ultraviolet radiation outside the target. A reflector defines a reflective surface and has an axis of reflection, a lamp produces radiation which has a wave length in the ultraviolet C range, and produces substantially no radiation in the ultraviolet A and B ranges, and the lamp is positioned so that a beam of concentrated indirect radiation is reflected from the reflector and extends outwardly along the axis of reflection, a collimator has a casing, closed side walls and opposed open ends, a plurality of plates in the casing are in spaced substantially parallel relation extending between the open ends substantially parallel to and coincident with the axis of reflection with the side walls positioned to cover entirely the side edges of the plates to cause the condensed beam to pass outwardly only through one of the open ends, a housing supports the collimator in alignment with the axis of reflection, and a positioning arrangement positions the housing so as to align the axis of reflection with the target area.

18 Claims, 8 Drawing Sheets

APPARATUS AND METHOD FOR PROJECTING GERMICIDAL ULTRAVIOLET RADIATION

BACKGROUND OF THE INVENTION

The present invention relates generally to devices for projecting germicidal ultraviolet radiation and, more particularly, to an apparatus and method for projecting a concentrated beam of germicidal ultraviolet radiation onto a preselected target area on the body of a patient undergoing surgery, without substantial emanation of ultraviolet radiation outside the target area.

The need for effective germicidal measures in the medical field is always present, in particular for orthopedic surgical procedures which expose vulnerable bone tissue to the air. The rate of infection of bone tissue in such procedures has long been an area of concern. Recent developments have made the need for effective germicidal measures even more pronounced, as a result of the increasing incidence of infection by virulent strains of antibiotic-resistant bacteria. As a consequence of the dangers presented by such antibiotic-resistant bacteria, it has also become necessary to reduce the general use of antibiotics, so as to minimize the opportunity for bacteria to mutate into resistant forms. Thus, efficient germicidal measures are highly desirable, both to reduce the present rate of infection in surgery and to allow the use of antibiotics to be scaled back.

Ultraviolet radiation has long been known to have a number of positive medical benefits, including highly effective germicidal properties, but is also known to have significant harmful effects including acting as a carcinogen, causing skin irritation and damaging of eye tissue. Thus, while ultraviolet radiation has a great potential for medical usefulness as a germicidal agent, its use has previously been limited by the inherent drawbacks and hazards involved.

Ultraviolet radiation can be generally divided into three components, each characterized by different wave lengths: ultraviolet A, ultraviolet B, and ultraviolet C. The germicidal effect is caused by ultraviolet C radiation, and specifically, radiation having a wave length of 253.7 nanometers. This component of ultraviolet radiation also is hazardous, and is known to cause skin inflammation which manifests itself as reddening of the skin surface without tanning. Additionally, and perhaps more significantly, overexposure to germicidal ultraviolet radiation results in eye inflammation and conjunctivitis, since the cornea of the eye is particularly vulnerable to ultraviolet C radiation. This inflammatory condition is known as photokeratitis, and while it ordinarily has no permanent effects, it can cause severe pain and discomfort to those affected.

Previous devices and methods have been developed in an attempt to provide for effective use of germicidal ultraviolet radiation while reducing the associated hazards, but none of these attempts have been entirely satisfactory. A number of previous germicidal ultraviolet radiation lamp designs make no provision for significantly controlling the radiation produced, but merely require that medical personnel either avoid any exposure to the radiation beam, or that they wear special protective gear including eye shields, hoods, and protective creams. For example, U.S. Pat. No. 2,274,298 to Koch discloses a portable sterilizing unit for generating germicidal ultraviolet radiation around a 360 degree expanse of the wall surfaces of a room. This device involves no radiation shielding of any kind, and personnel apparently must vacate the area of use to avoid exposure to the germicidal ultraviolet radiation.

U.S. Pat. No. 4,909,254 to Wilkinson discloses a method and apparatus for ultraviolet radiation phototherapy of skin wounds which includes directing ultraviolet A and ultraviolet C radiation at the wound area. The Wilkinson device and method involves filtering out the ultraviolet B component from ultraviolet radiation produced by the device, leaving both the ultraviolet A and ultraviolet C components in the radiation. The Wilkinson device also includes a provision for focusing the resulting ultraviolet A and ultraviolet C radiation beam on the wound, but makes no provision for significant control of the beam so as to prevent ultraviolet radiation from emanating outside the wound area, thereby potentially exposing attending personnel to ultraviolet radiation with all of its harmful effects.

A medical study presented in the paper "Ultraviolet Radiation: Its Beneficial Effect on the Operating Environment in the Incident of a Deep Wound Infection Following Total Hip and Total Knee Arthroplasty," by Doctors Lowell and Kundsin, was conducted using ultraviolet radiation lamps to irradiate a large operating room area, with a protocol requiring all personnel in the operating room to wear eye shields, hoods, and protective cream. While the use of germicidal ultraviolet radiation in the study significantly decreased post-operative infections, the use of these lamps necessitated significant protective measures, and despite these measures three cases of conjunctivitis were caused in members of the operating team by lack of proper eye shielding.

A different approach is illustrated by the Lumalier products of Commercial Lighting Design, Inc., which provide supplemental air disinfection by germicidal ultraviolet radiation in the upper reaches of a room. These devices project ultraviolet radiation into the upper portion of a room, while shielding the lower portion where personnel would ordinarily be located. This shielding is accomplished through a collimator having essentially open side walls to widely disperse the ultraviolet radiation horizontally while generally preventing it from reaching the lower part of the room. The Lumalier devices are designed with essentially open side walls so that they produce a fan-shaped radiation pattern, as opposed to a limited, defined beam. These fixtures must generally be located at least seven feet above the floor in order to effectively shield occupants of the room. The Lumalier devices are apparently capable of reducing the number of germs in the upper portion of a room, but can only act on germs which reach the upper part of the room. Infectious material on lower surfaces is entirely unaffected by the devices unless carried upward into the irradiated area.

None of the above-described devices and methods can be safely used in an operating room to reduce or eliminate germs within a specific target area on a patient during surgery without requiring extensive and inconvenient protective measures for the operating room personnel and the patient. The germicidal effects of ultraviolet radiation are, however, highly beneficial, as demonstrated in the paper by Lowell and Kundsin, and a need therefore exists for a safe and convenient device and method for the use of germicidal ultraviolet radiation during surgery.

SUMMARY OF THE INVENTION

In accordance with the present invention, an apparatus and method are provided for projecting a concentrated beam of germicidal ultraviolet radiation onto a preselected target area on the body of a patient undergoing surgery, without substantial emanation of ultraviolet radiation outside the target area. The apparatus of the present invention comprises a reflector defining a reflective surface and having an axis of reflection, a lamp for producing germicidal radiation which has a wavelength in the ultraviolet C range, and substantially no radiation in the ultraviolet A and B ranges, the lamp being positioned so that a beam of concentrated indirect radiation is reflected from the reflector and extends outwardly along the axis of reflection. The apparatus also includes a collimator having a casing formed by closed side walls and opposite open ends, and a plurality of plates mounted within the casing in spaced substantially parallel relation to one another and extending between the open ends in a direction substantially parallel to and coincident with the axis of reflection with the side walls positioned to cover entirely the side edges of the plates, to thus cause the condensed beam to pass outwardly only through one of the open ends. A housing is provided for supporting the collimator in alignment with the axis of reflection, and a positioning arrangement is provided for positioning the housing so as to align the axis of reflection with the target area, whereby the concentrated beam of indirect germicidal ultraviolet radiation is projected onto the target area on the patient's body without substantial emanation of ultraviolet radiation outside thereof.

The apparatus preferably includes a radiation redirecter positioned intermediate the lamp and the collimator to reflect direct radiation from the lamp onto the reflective interior of the reflector. The reflective surface of the reflector preferably has an elliptical contour forming a channel having a longitudinal axis which is substantially normal to the axis of reflection and substantially parallel to the plates.

A preferred embodiment of the invention preferably may include a sensor mounted in the reflector for sensing the intensity of ultraviolet radiation produced by the lamp, and an alarm arrangement for producing an alarm signal if the sensed intensity varies from a preselected range.

In a preferred embodiment, the apparatus may include a plurality of substantially parallel spaced dividers positioned intermediate the plates and extending substantially parallel to the axis of reflection between the open ends. The plates and dividers of the present invention preferably are coated with a non-reflective matte black powder finish.

In a preferred embodiment, the germicidal ultraviolet radiation projecting apparatus includes two visible light lamps mounted on opposing sides of the collimator and aligned with the axis of reflection for accurate aiming of the condensed beam of radiation. The beam of radiation has a predetermined optimal range of projection within which the beam has optimal effectiveness and the beams of visible lights are focused at the optimal range of projection so that the apparatus can be positioned with the beams of visible lights focused on the target area to insure that the target area is within the optimal range of projection.

The present invention's method for projecting a beam of germicidal ultraviolet radiation onto a preselected target area on the body of a patient undergoing surgery comprises the steps of providing a germicidal ultraviolet radiation projector having a reflector with an axis of reflection and a collimator coincident and aligned with the axis of reflection, aligning the axis of reflection with the target area, directing germicidal ultraviolet radiation having a wave length in the ultraviolet C range, and substantially no radiation in the ultraviolet A and B ranges, at the reflector, condensing the ultraviolet radiation into a beam on the reflector, reflecting the beam of radiation from the reflector and directing it into the collimator, absorbing in the collimator a portion of the beam of radiation which is not traveling in a path substantially aligned with the axis of reflection, and projecting the remaining portion of the beam of condensed indirect ultraviolet radiation from the collimator to the target area, whereby undesired germs at the target area on the body of the patient are destroyed without substantial emanation of ultraviolet radiation outside the target area.

Accordingly, the present invention provides an apparatus and method for safely and effectively projecting a beam of germicidal ultraviolet radiation onto a target area on the body of a patient undergoing surgery, so that undesired germ material is killed without the patient and other personnel in the operating room being exposed to hazardous ultraviolet radiation.

DESCRIPTION OF THE PREFERRED EMBODIMENT

Figure 1:
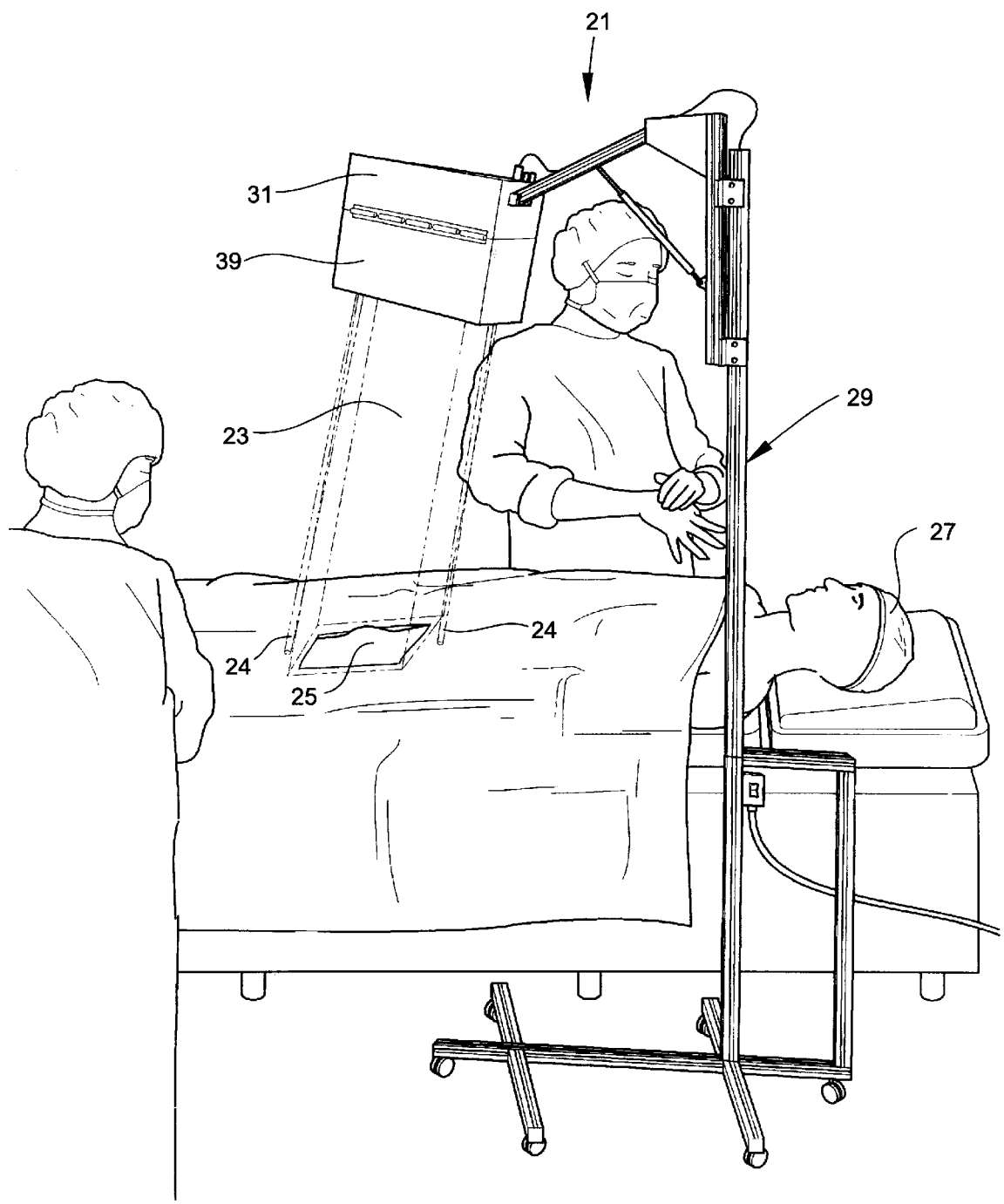
FIG. 1 is a perspective view of the preferred embodiment of the germicidal ultraviolet radiation projecting apparatus of the present invention shown in use during surgery on a patient.

Looking now in greater detail at the accompanying drawings, FIG. 1 illustrates in perspective view the germicidal ultraviolet radiation projecting apparatus 21 of the present invention in use to project to a radiation beam 23 onto a target area 25 on the body of a patient 27 undergoing surgery. The present invention provides highly effective germicidal action at the target area 25, which may be the location of an incision to be made during orthopedic surgery as shown in FIG. 1. Germicidal action is particularly important for orthopedic surgery of this type in which bone tissue will be exposed, since such bone tissue is highly vulnerable to infection. As used herein, "surgery" is meant to reference all medical procedures which involve the exposure of tissue below the external layer of skin, including the treatment of wounds. The usefulness of the present invention extends to the field of veterinary medicine, and "patient" is intended to include the subjects of veterinary treatment.

Ultraviolet radiation projecting apparatus 21 is mounted on a portable and adjustable stand 29, so that it can be quickly positioned to project radiation beam 23 onto the target area 25. The stand 29 also allows radiation projecting apparatus 21 to be readily positioned at the appropriate distance from the target area 25 for optimal effectiveness and safe operation.

Figure 2:
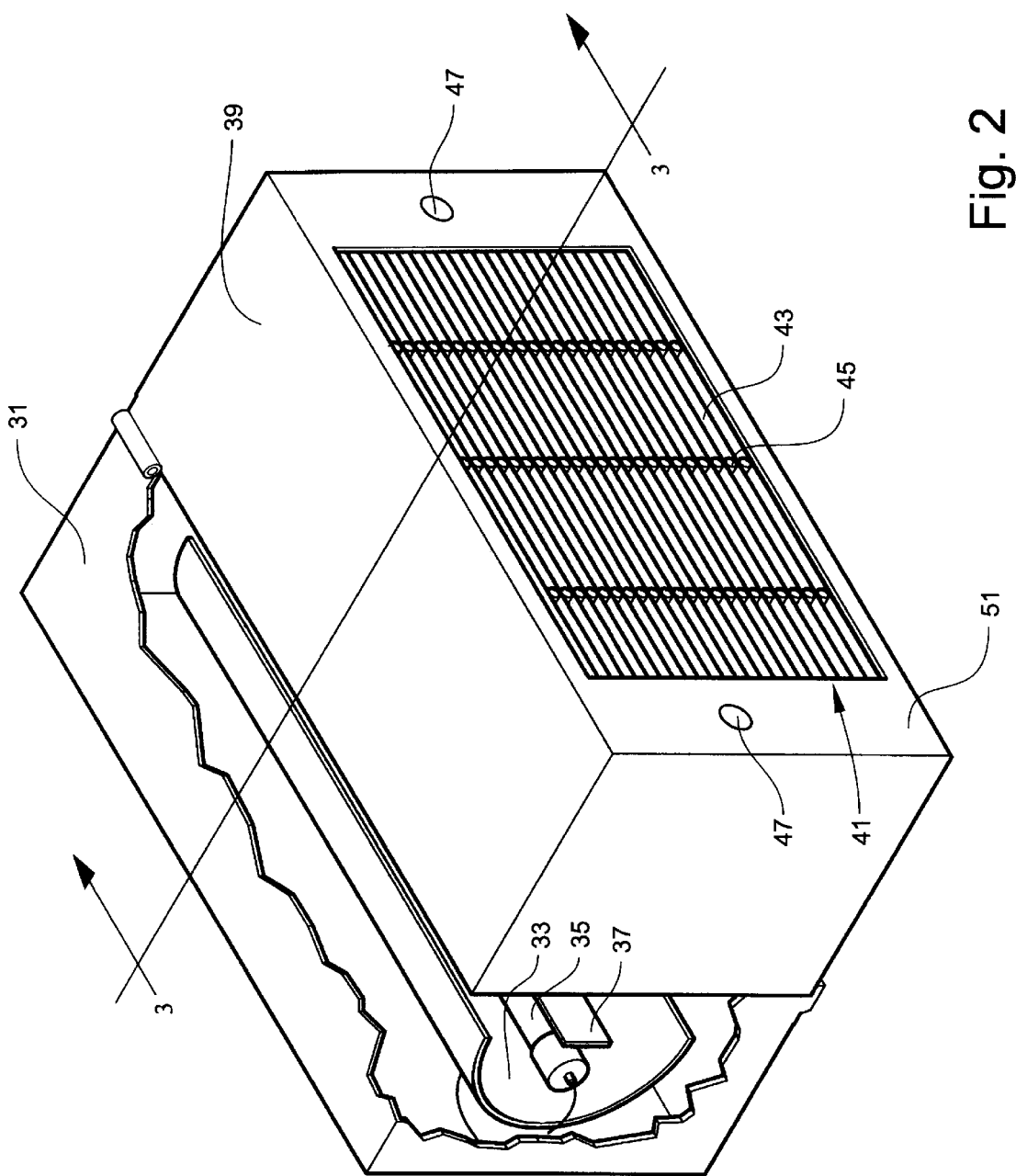
FIG. 2 is an isometric view of the ultraviolet radiation projecting apparatus of FIG. 1, partially cut away to show the reflector, lamp, and redirector of the present invention.

FIG. 2 shows the radiation projecting apparatus 21 with a portion of reflector housing 31 cut away, so that reflector 33, lamp 35 and reflective radiation redirector 37 can be partially seen. A collimator housing 39 contains a collimator 41, which includes plates 43 and dividers 45. Apertures 47 for visible light aiming and focusing lamps 49 (see FIG. 5), are formed in front face 51 of the collimator housing 39, and will be described in greater detail presently.

Figure 3:
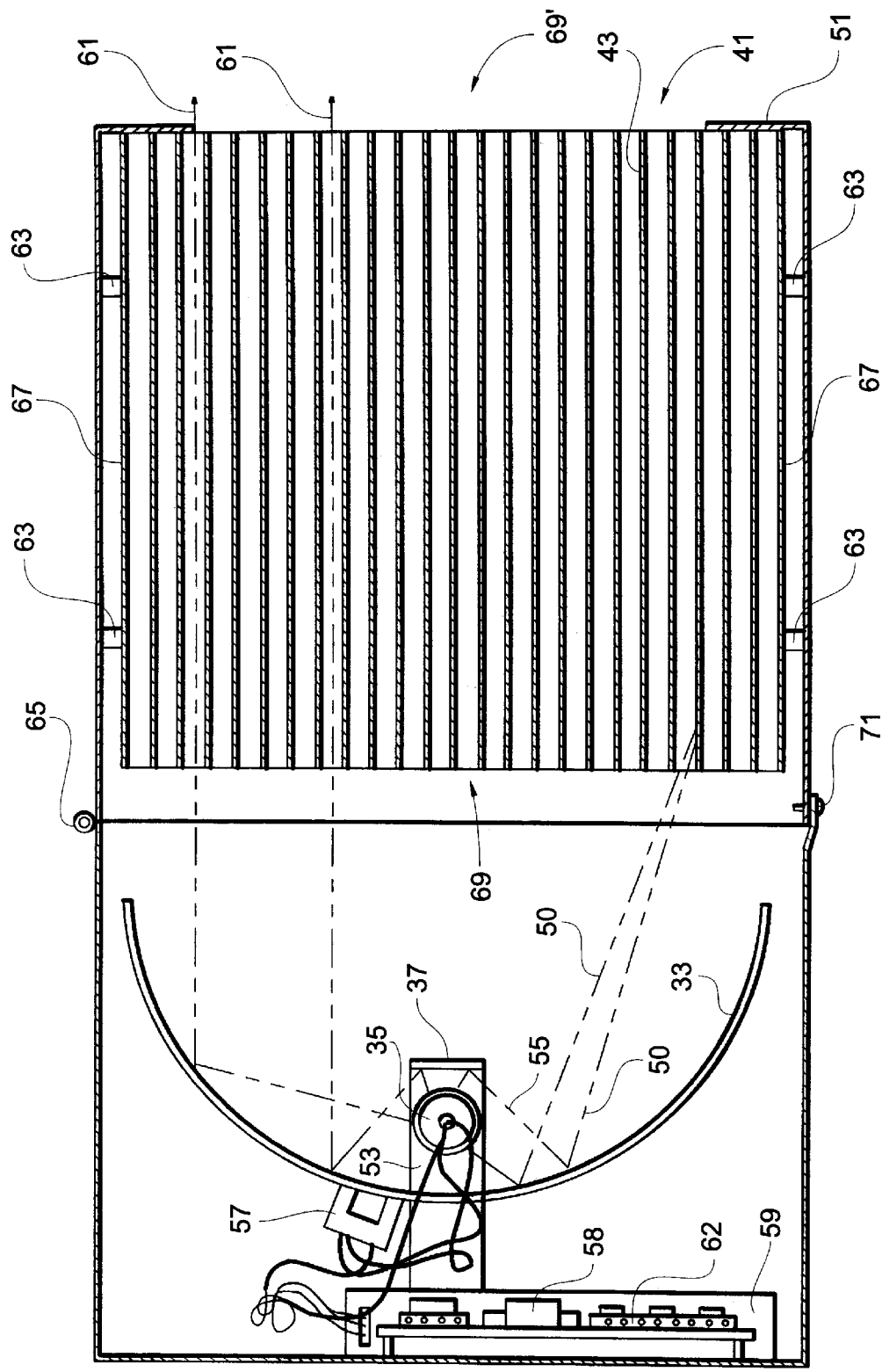
FIG. 3 is a cross-sectional view of the present ultraviolet radiation projecting apparatus of FIG. 1, taken along line 3—3 of FIG. 2.
Figure 4:
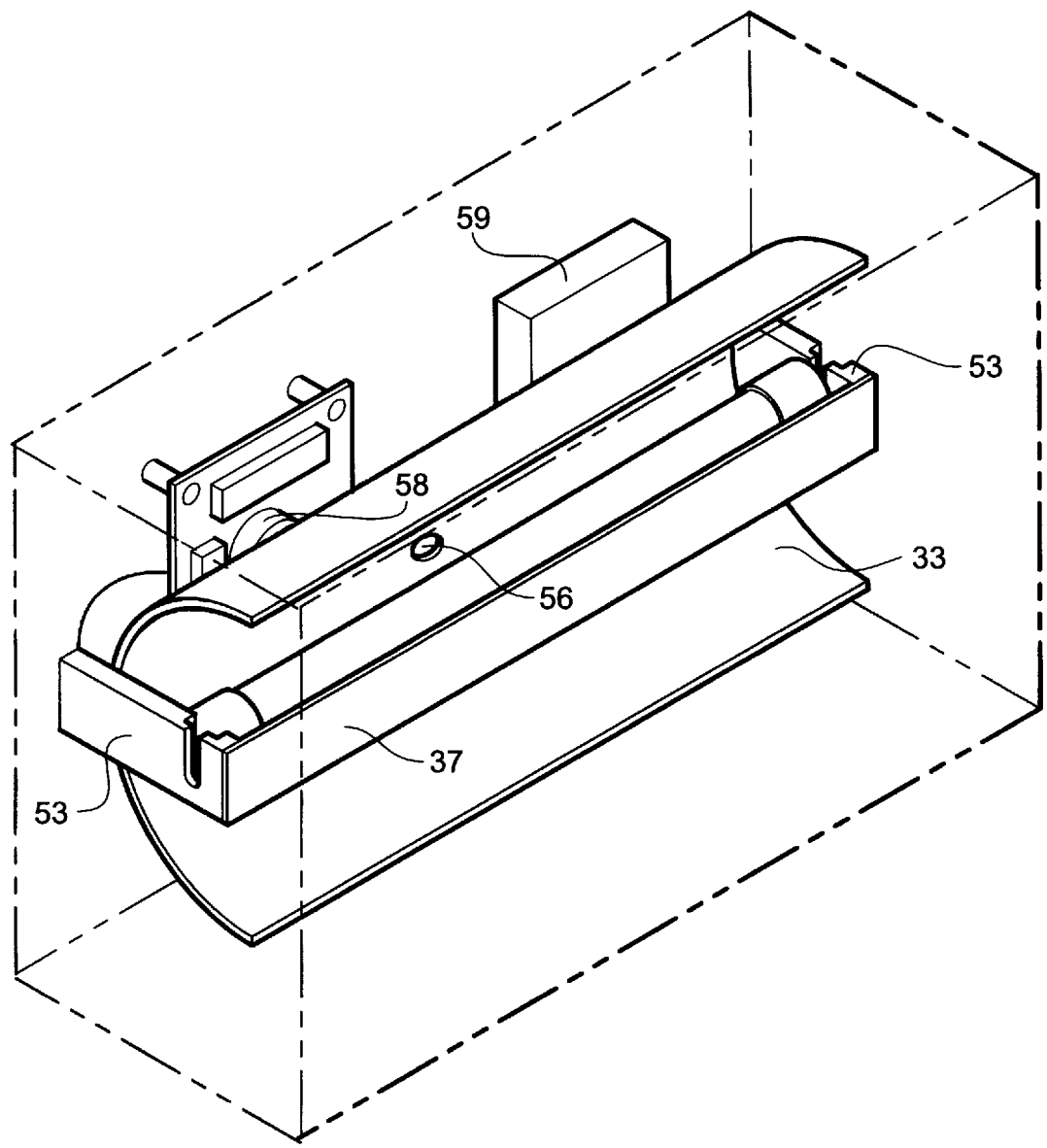
FIG. 4 is an isometric view of the reflector, lamp, and redirector of the present invention with the housing not shown to more clearly illustrate such components.

The details of the reflector 33, lamp 35, and redirector 37, of the present invention are shown in greater detail in FIGS. 3 and 4. The reflector 33 forms a longitudinal channel having a reflective interior surface and forms an arcuate contour. As shown in FIG. 3, the reflector 33 forms an elliptical contour, and lamp 35 is located within the reflective interior of reflector 33 and is held in place by brackets 53. Reflective redirector 37 is also mounted on brackets 53, and is positioned intermediate lamp 35 and collimator 41 so as to prevent direct radiation from lamp 35 from entering collimator 41, and to reflect such direct radiation, as shown by radiation wave 55, back onto the reflector 33 from where it may be reflected into the collimator 41. Dividers 45 and visible light lamp 49 have been omitted from FIG. 3 for clarity, but may be seen in FIG. 5.

A conventional ultraviolet radiation sensor 57 is mounted on the reflector 33 to provide monitoring of the intensity of the ultraviolet radiation produced by the lamp 35, and directed to sensor 57 though sensor aperture 56 (see FIG. 4). Sensor model OSD5.8-7-Q from Centronic Inc., may be employed for this purpose. A conventional alarm 58 is connected to sensor 57 to provide an alarm signal when certain levels of radiation are sensed, and will be described below. A ballast 59, and its associated components provide and regulate electricity to power the lamp 35. At least a portion of the radiation waves reflected off of the reflector 33 travel along the reflector's axis of reflection as shown by radiation waves 61. This axis of reflection is oriented as illustrated by waves 61 in FIG. 3, and is also perpendicular to the longitudinal axis of the reflector 33.

The plates 43 of the collimator 41 are oriented and spaced in a substantially parallel arrangement, and in a preferred embodiment are 0.282 inches apart from each other. The plates may be 0.032 inch thick aluminum plates measuring 6 inches by 12 inches. The plates 43 are also oriented substantially parallel to the axis of reflection of the reflector 33 as illustrated in FIG. 3. Braces 63 in the collimator housing 39 assist in properly positioning the collimator 41 so that each of the plates 43 lie in a plane substantially parallel to the axis of reflection as represented by radiation waves 61.

Figure 5:
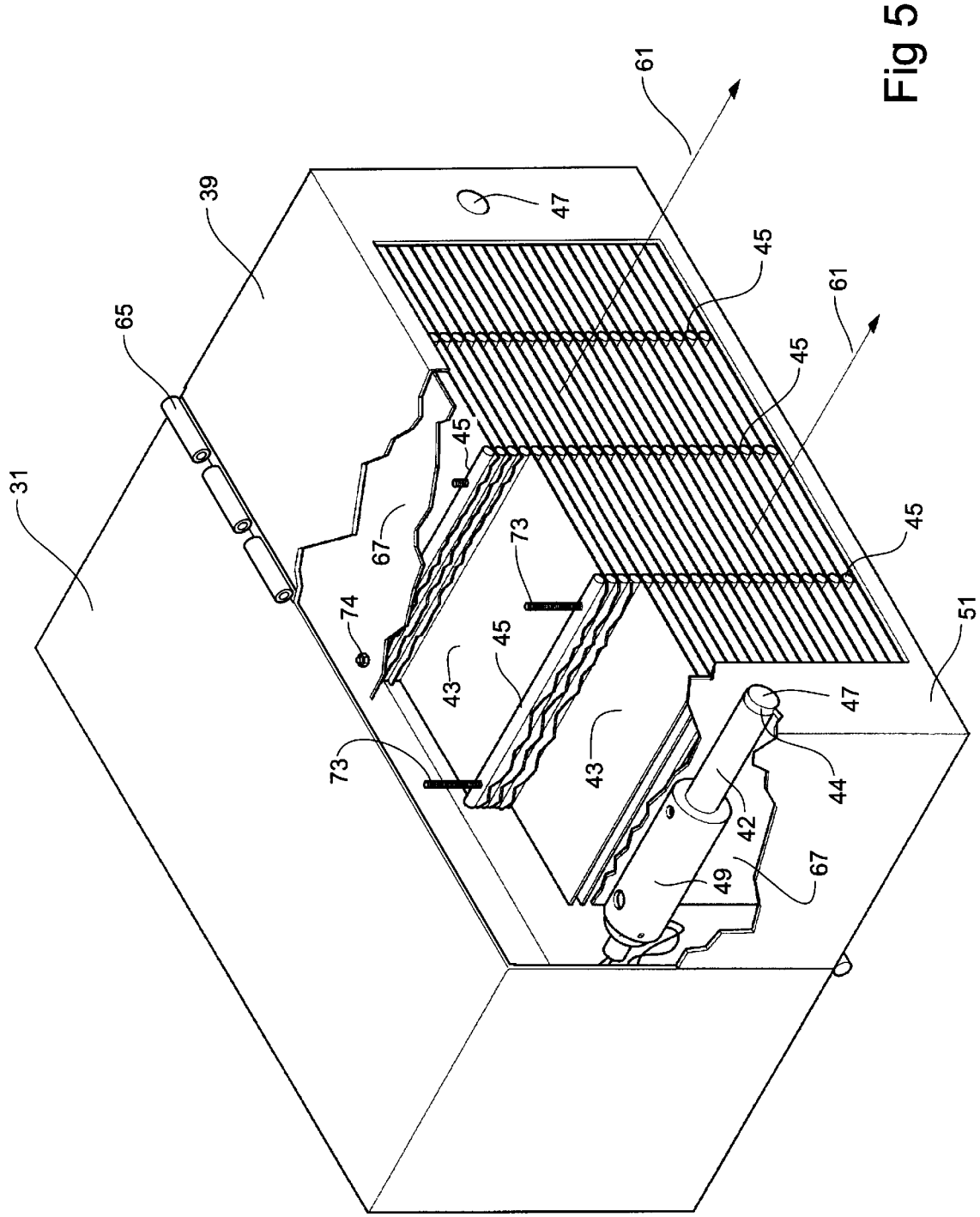
FIG. 5 is an isometric view of the radiation projecting apparatus of FIG. 1, partially cut away to depict individual components thereof.
Figure 6:
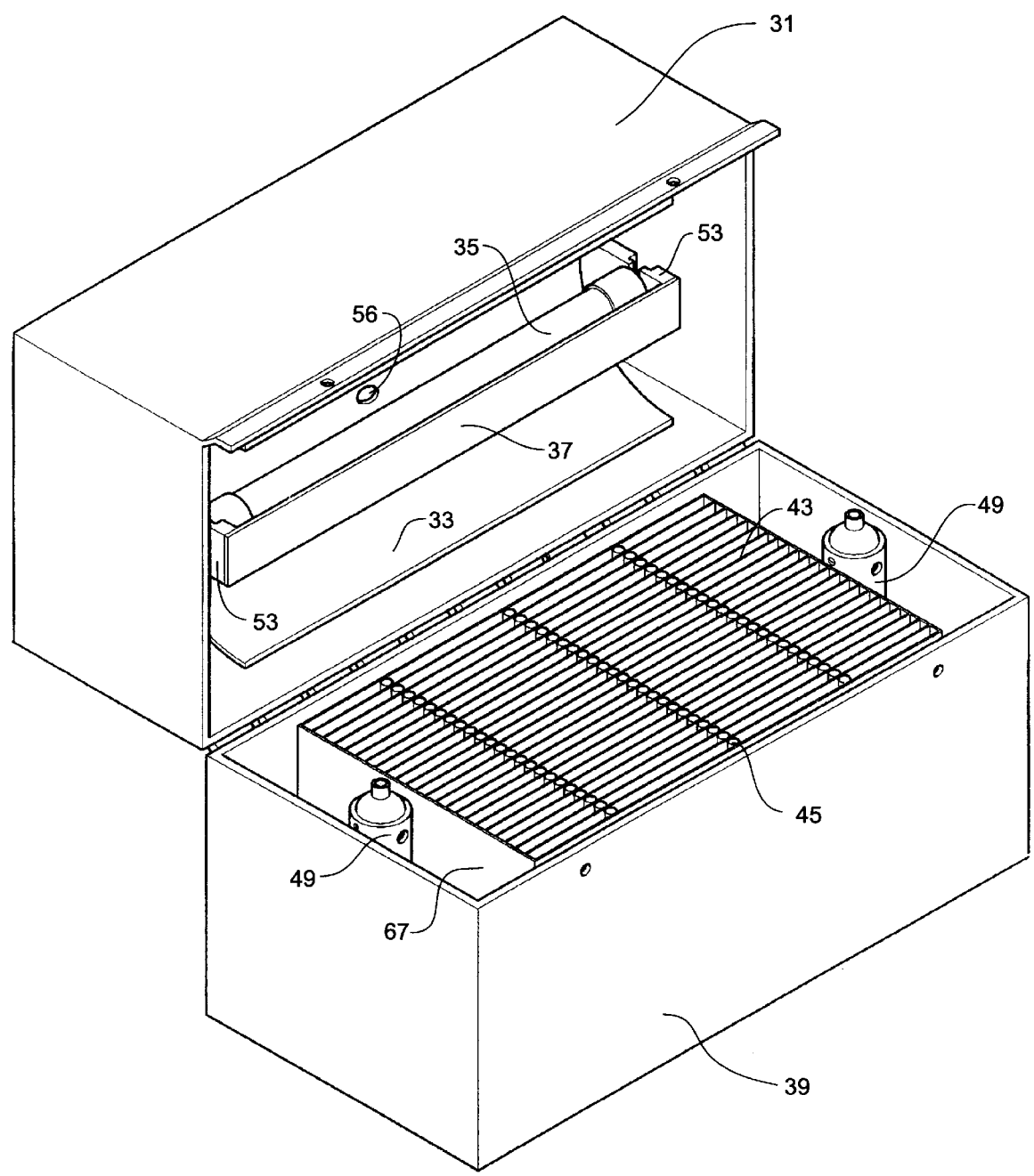
FIG. 6 is an isometric view of the radiation projecting apparatus showing the two housing portions separated along their hinge to permit access to the interior of the apparatus.

The collimator 41 is enclosed on its four rectangular sides 67, two of which are partially shown in FIG. 5, and open at its two opposed ends 69, 69' (see FIG. 3) to, respectively, receive the radiation beam from the reflector 33 and to project the radiation beam 23 outwardly along the axis of reflection. The collimator housing 39 is connected to the reflector housing 31 by hinge 65 and set screw 71 (see FIG. 3), which may be removed to allow opening of the two housing portions about hinge 65 as shown in FIG. 6.

As best seen in FIG. 5, the plates 43 of the collimator 41 are separated by dividers 45 and enclosed by the aforesaid collimator side walls 67. The components of the collimator 41 are joined by threaded rods 73 which may be composed of aluminum or other suitable material, and are secured by nuts 74, or other appropriate conventional fasteners. Threaded rods 73 are inserted through holes conventionally drilled in the plates 43, the dividers 45, and the side walls 69, so as to effectively tie together all the components of the collimator 41. The plates 43, the dividers 45, and the side walls 69 all have non-reflective surfaces, and are all preferably coated with a matte black powder finish. The dividers 45 may be tubular in form, as shown in FIG. 5, or may form another geometric shape, so long as the dividers 45 extend substantially the entire distance between the plates 43 so as to prevent radiation from passing from one side of the dividers 45 to the other side. Threaded rods 73 pass through the interior of dividers 45 thereby substantially blocking the passage of ultraviolet radiation through the open interior of the dividers.

Visible light aiming and focusing lamps 49 are mounted in the collimator housing 39 on opposing sides of the collimator 41, and apertures 47 are positioned in the front face 51 of the collimator housing to allow the light beams produced by visible light lamps 41 to project outwardly. Visible light lamps 49 are preferably 12 volt halogen lamps rated at 20 watts, and they are oriented to project beams 24 parallel to the axis of reflection of the reflector 33 and configured by conventional focusing tubes 42 and lens 44 to produce a sharply focused field of light at points located between 36 inches and 44 inches from the front face 51.

In operation, the lamp 35 produces ultraviolet C radiation primarily at the germicidal wave length of 253.7 nanometers, and substantially no radiation in the ultraviolet A and B ranges. The ballast 59 for the lamp 35 is preferably a 35 watt metal halide electronic ballast and operates on 110–115 volt AC current to drive the lamp 35 at 0.35 amps.

In a preferred embodiment, lamp 35 is a low pressure mercury arc lamp with a tubular envelope, and may be rated at 8 watts, with a 50 watt adjustable resistor in the circuit between lamp 35 and ballast 59.

In the event that the lamp 35 produces ultraviolet radiation having an intensity either below or above an acceptable range, the sensor 57 will detect this variance and cause alarm 58 to produce a signal to alert an operator. The alarm signal can include warning lights and an audible warning signal. For example, sensor 35 can be of a type producing low voltage DC current in response to sensed intensity, and can be set to trigger alarm 58 if it senses an intensity corresponding to a level below 22 mW/cm$^2$ at 40 inches from front face 51, or above 30 mW/cm$^2$ at the same distance. In a preferred embodiment, conventional electronics controller 62 monitors sensor 35 and controls alarm 58, while also controlling the output of ballast 59. A conventional switch (not shown) may also be employed in connection with electronic controller 62 to allow selective adjustment of the intensity of radiation produced by lamp 35.

The ultraviolet radiation produced by the lamp 35 is reflected off of the reflector 33 and condensed into a beam of ultraviolet radiation, which is directed to the open back end 69 of the collimator 41 along the axis of reflection of the reflector 33. Direct radiation from the lamp 35 is prevented from entering the collimator 41, as noted above, by the reflective redirector 37. The radiation beam entering the collimator 41 consists of ultraviolet radiation waves traveling generally aligned with the axis of reflection of the reflector 33, but also includes some radiation waves 50 (see FIG. 3) which diverge from this axis. Radiation waves which are not aligned with the axis of reflection enter the collimator 41 and are either absorbed or redirected by the non-reflective surfaces of the plates 43 and the dividers 45 in the collimator 41. Thus, the condensed beam of ultraviolet radiation which is projected outwardly from the open front end 69' of the collimator 41 consists entirely of radiation waves which are substantially aligned with the axis of reflection.

The contour of the reflection surface of the reflector 33 can be modified and the placement of the lamp 35 altered so as to create condensed beams of ultraviolet radiation having differing characteristics.

Figure 7:
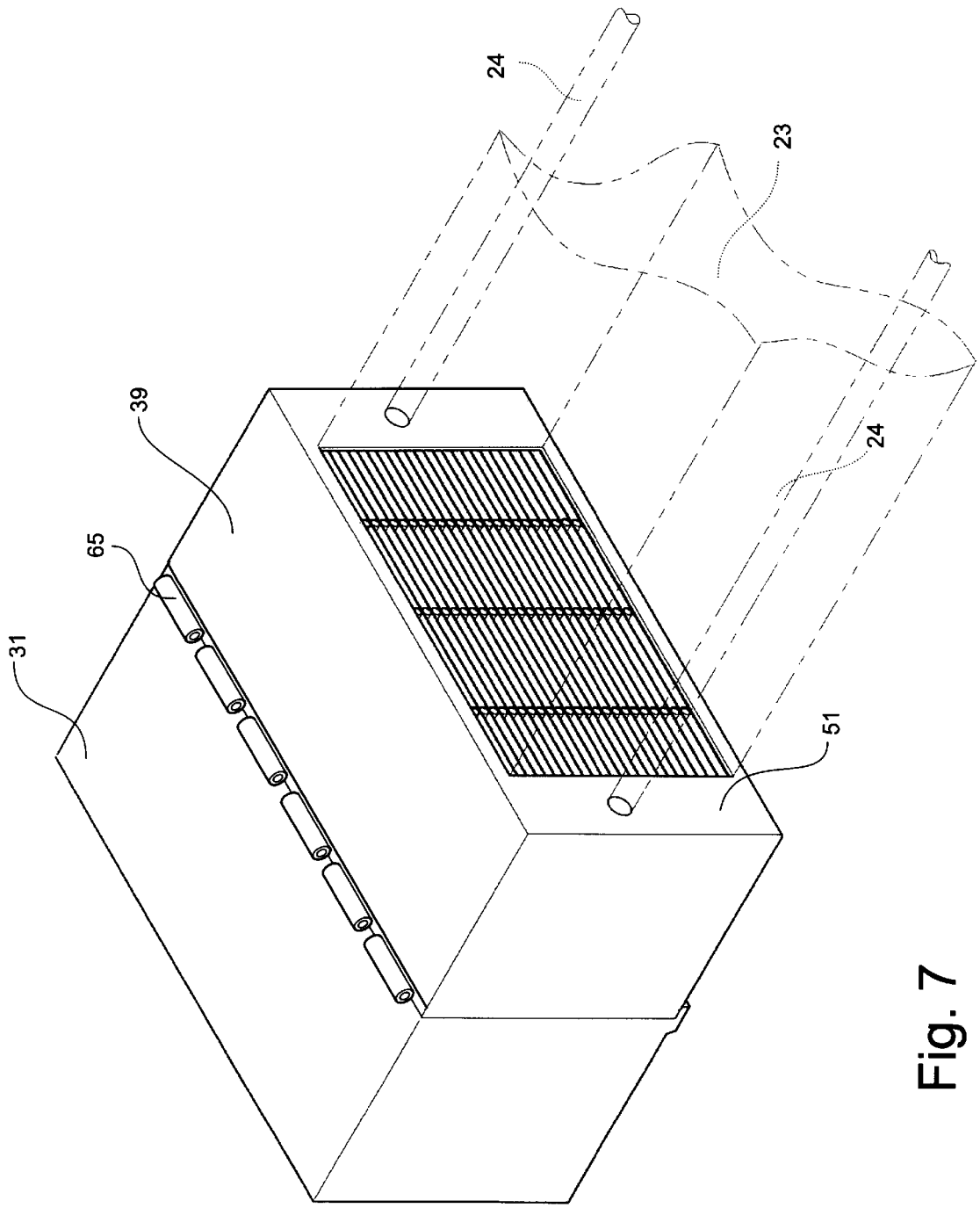
FIG. 7 is an isometric view of the ultraviolet radiation projecting apparatus of the present invention depicting the ultraviolet radiation beam and visible light aiming and focusing beams projecting outwardly therefrom.

The condensed beam 23 of germicidal ultraviolet radiation projected from the collimator 41 is shown in FIG. 7, along with visible light beams 24 generated by the lamps 49. Over its optimal range of projection, which is approximately 36 inches to 44 inches from the front face 51 of the collimator housing 39, the condensed radiation beam 23 does not disperse significantly from a cross-sectional area of approximately 6 inches by 12 inches. The consistent shape of the beam 23 results from the substantially parallel alignment of the ultraviolet radiation waves making up the beam 23 after it has passed through the collimator 41, in which divergent waves 50 are either absorbed or redirected in such a manner that any such waves leaving the collimator will be within the radiation beam 23.

The compact shape and substantially parallel alignment of the radiation beam 23 over its optimal range of projection therefore insures that substantially no ultraviolet radiation will emanate or be projected outside the target area 25. Thus, the germicidal ultraviolet radiation projecting apparatus 21 can be employed in an operating room as shown in FIG. 1, without requiring medical personnel and the patient to wear protective eye shields, use protective cream, or wear extensive protective clothing. The present invention therefore significantly enhances the convenience and ease of use of germicidal ultraviolet radiation, while still maintaining a high degree of germicidal effectiveness.

Figure 8:
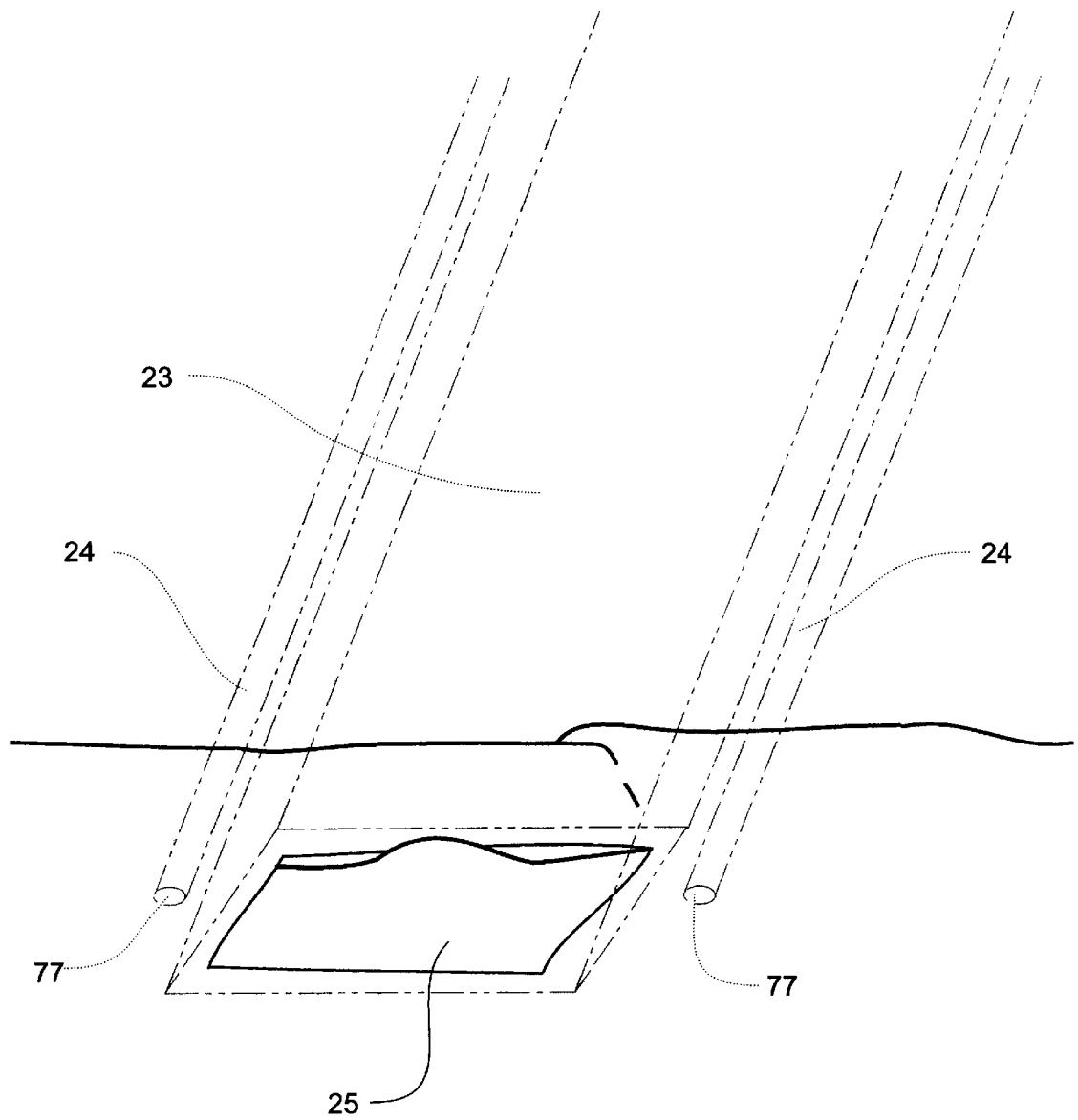
FIG. 8 is a detailed view depicting the target area on the patient, the radiation beam as it reaches the target area, and the visible light aiming and focusing beams.

In use, the ultraviolet radiation projecting apparatus 21 must be accurately aligned with the target area 25 and positioned at a correct distance from the target area. The radiation beam 23 itself is not visible, and is of no assistance in the aiming process. Aiming and focusing visible light lamps 49 are therefore provided to allow the radiation projecting apparatus 21 to be accurately positioned. Visible light beams 24 are projected from front face 51 on opposing sides of collimator 41 and radiation beam 23, as shown in FIG. 7, and are also aligned parallel with the axis of reflection of reflector 33 and, therefore, also parallel to the radiation beam 23. Thus, aiming of the radiation projecting apparatus 21 is accomplished by positioning the stand 29 and housing portions 31, 39 so that visible light beams 24 are oriented on opposing sides of the target area 25, as shown in FIG. 1. In FIG. 8, the position of visible light beams 24 can be seen more clearly, as can the patterns 77 of visible light formed adjacent the target area 25 by the beams 24.

Radiation beam 23 also must be positioned an appropriate distance from the target area 25 so that the target area is within the optimal range of projection for the radiation beam, which in the preferred embodiment consists of an 8 inch deep region located between 36 inches and 44 inches from front face 51. A target area surface within this optimal range will be exposed to between 24 and 28 mW/cm$^2$ of germicidal ultraviolet radiation evenly across the width of radiation beam 23, with substantially no emanation of ultraviolet radiation outside the target area. This dosage of germicidal ultraviolet radiation is considered to be optimal for its effect in destroying undesired germ material. Moreover, the eight inch depth of the optimal range allows the radiation beam 23 to reach into a surgical incision for germicidal effect within the opening created by the incision. The ability to project germicidal ultraviolet radiation inside an incision is highly desirable for many orthopedic surgical procedures which expose bone tissue that is extremely vulnerable to infection by the ambient air as described above, and effective germicidal action thereon is of significant medical advantage.

Correct alignment of the target area 25 within the optimal range of projection of radiation beam 23 is accomplished through the use of visible light lamps 49, and, as described above light beams 24 are focused so that they produce sharply defined patterns 77 on illuminated surfaces which are located at the optimal range of projection. Thus, while the radiation beam 23 itself cannot be seen, visible light lamps 49 allow accurate and precise positioning of germicidal radiation beam 23 on the target area 25 and at an appropriate distance for safe operation and optimal germicidal effect.

The germicidal ultraviolet radiation projecting apparatus and method of the present invention has several significant advantages. The highly beneficial germicidal effects of ultraviolet radiation can be harnessed to generally reduce the incidence of infections resulting from medical procedures, while the use of antibiotics can also potentially be scaled back, possibly minimizing the occurrence of virulent antibiotic-resistant bacteria strains. During use of the germicidal ultraviolet radiation projecting apparatus and method of the present invention, however, medical personnel need not take extensive precautions to prevent exposure to the ultraviolet radiation. Eye shields, extensive protective clothing, and protective creams are not required during the course of an operation of ordinary duration.

The condensed beam of indirect ultraviolet radiation produced by the present invention does not emanate substantial amounts of ultraviolet radiation outside the intended target area, and therefore does not expose individuals outside the target area to significant amounts of the ultraviolet radiation. The condensed beam produced by the present invention, with its restricted pattern, thus does not disperse over a wide area as do the beams produced by devices such as the Lumalier products, which are designed to irradiate large portions of a room. The visible light aiming and focusing lamps of the present invention allow the ultraviolet radiation projecting apparatus to easily be positioned at the correct location for safe and effective germicidal effect.

It will therefore be readily understood by those persons skilled in the art that the present invention is susceptible of broad utility and application. Many embodiments and adaptations of the present invention other than those herein described, as well as many variations, modifications and equivalent arrangements will be apparent from or reasonably suggested by the present invention and the foregoing description thereof, without departing from the substance or scope of the present invention. Accordingly, while the present invention has been described herein in detail in relation to its preferred embodiment, it is to be understood that this disclosure is only illustrative and exemplary of the present invention and is made merely for purposes of providing a full and enabling disclosure of the invention. The foregoing disclosure is not intended or to be construed to limit the present invention or otherwise to exclude any such other embodiments, adaptations, variations, modifications and equivalent arrangements, the present invention being limited only by the claims appended hereto and the equivalents thereof.

I claim:

1. An apparatus for projecting a beam of germicidal ultraviolet radiation onto a preselected target area on the body of a patient undergoing surgery, comprising:

a reflector defining a reflective surface and having an axis of reflection;

a lamp for producing germicidal radiation having a wavelength in the ultraviolet C range, and substantially no radiation in the ultraviolet A and B ranges, said lamp being positioned so that a condensed beam of ultraviolet radiation is reflected from said reflector and extends outwardly along said axis of reflection;

a collimator having a casing formed by closed side walls and opposed open ends, and a plurality of plates mounted within said casing in spaced substantially parallel relation to one another and extending between said open ends in a direction substantially parallel to and coincident with said axis of reflection with said side walls positioned to cover the side edges of said plates to cause said condensed beam to pass outwardly only through one of said open ends;

housing means for supporting said collimator in alignment with said axis of reflection; and positioning means for positioning said housing to align said axis of reflection with the target area, whereby the condensed beam of indirect germicidal ultraviolet radiation is projected onto the target area on the patient's body without substantial emanation of ultraviolet radiation outside thereof.

2. The germicidal ultraviolet radiation projecting apparatus of claim 1, further including a radiation redirector, said redirector being positioned intermediate said lamp and said collimator so as to reflect direct radiation from said lamp onto said reflective interior of said reflector.

3. The germicidal ultraviolet radiation projecting apparatus of claim 1, wherein said reflective surface of said radiation reflector has an arcuate contour that forms a channel having a longitudinal axis.

4. The germicidal ultraviolet radiation projecting apparatus of claim 3, wherein said longitudinal axis is substantially normal to said axis of reflection and substantially parallel to said plates.

5. The germicidal ultraviolet radiation projecting apparatus of claim 1, wherein said reflective surface of said radiation reflector has an elliptical contour that forms a channel having a longitudinal axis.

6. The germicidal ultraviolet radiation projecting apparatus of claim 1, further including a sensor for sensing the intensity of ultraviolet radiation produced by said lamp, and wherein said sensor includes an alarm means for producing an alarm signal when the sensed intensity varies from a preselected range.

7. The germicidal ultraviolet radiation projecting apparatus of claim 1, wherein said plates have non-reflective outer surfaces.

8. The germicidal ultraviolet radiation projecting apparatus of claim 7, wherein said outer surfaces of said plates are coated with a matte black powder finish.

9. The germicidal ultraviolet radiation projecting apparatus of claim 1, further including a plurality of substantially parallel spaced dividers positioned intermediate said plates and extending substantially parallel to said axis of reflection between said open ends.

10. The germicidal ultraviolet radiation projecting apparatus of claim 9, wherein said plates and said dividers have non-reflective outer surfaces.

11. The germicidal ultraviolet radiation projecting apparatus of claim 1, further including aiming means for projecting a beam of visible light aligned with said axis of reflection for permitting the beam of ultraviolet radiation to be accurately aimed.

12. The germicidal ultraviolet radiation projecting apparatus of claim 11, wherein said aiming means includes two visible light lamps mounted on opposing sides of said collimator.

13. The germicidal ultraviolet radiation projecting apparatus of claim 1, wherein the condensed beam of radiation from said collimator has a predetermined optimal range of projection within which the condensed beam has optimal effectiveness, and further including focusing means for projecting a beam of visible light focused at the optimal range of projection and aligned with said axis of reflection, whereby said housing can be positioned so that said beam of visible light is focused on the target area and the target area is within the optimal range of projection.

14. The germicidal ultraviolet radiation projecting apparatus of claim 10, wherein said outer surfaces of said plates and said dividers are coated with a matte black powder finish.

15. The germicidal ultraviolet radiation projecting apparatus of claim 1, wherein said housing includes a reflector enclosing portion and a collimator supporting portion, and said housing portions are hingedly connected, said housing portions having a closed position in which said collimator is aligned with said reflector and an open position wherein said collimator supporting portion is pivoted away from said reflector enclosing portion, said housing further including locking means for selectively locking said housing portions in said closed position.

16. The germicidal ultraviolet radiation projecting apparatus of claim 1, wherein said lamp has a tubular envelope.

17. The germicidal ultraviolet radiation projecting apparatus of claim 1, wherein said lamp is a low pressure mercury arc lamp.

18. An apparatus for projecting a beam of germicidal ultraviolet radiation onto a preselected target area on the body of a patient undergoing surgery, comprising:

a reflector defining a reflective surface and having an axis of reflection, said reflective surface having an elliptical contour forming a channel having a longitudinal axis normal to said axis of reflection;

a tubular low pressure mercury arc lamp for producing germicidal radiation having a wavelength in the ultraviolet C range, and substantially no radiation in the ultraviolet A and B ranges, said lamp being positioned to provide a beam of condensed indirect radiation reflected from said reflector and extending outwardly along said axis of reflection;

a sensor located in said reflector for sensing the intensity of ultraviolet radiation produced by said lamp, said sensor including alarm means for producing an alarm signal when said sensed intensity varies from a predetermined range;

a collimator having a casing formed by closed side walls and opposed open ends, and a plurality of plates mounted within said casing in spaced substantially parallel relation to one another and extending between said open ends in a direction substantially parallel to and coincident with said axis of reflection with said side walls positioned to cover entirely the side edges of said plates to cause said condensed beam to pass outwardly only through one of said open ends;

a plurality of substantially parallel spaced dividers positioned intermediate said plates and extending substantially parallel to said axis of reflection between said open ends;

said plates and said slats being coated with a non-reflective matte black finish;

a reflective radiation redirector, said redirector being positioned intermediate said lamp and said collimator so as to reflect direct radiation from said lamp onto said reflective interior of said reflector;

housing means for supporting said collimator in alignment with said axis of reflection;

a pair of visible light lamps mounted in said housing on opposing sides of said collimator, each said lamp producing a beam of visible light aligned with said axis of reflection and focused at said optimal range of projection; and positioning means for positioning said housing to align said beams of visible light with the target area and in focused disposition on the target area, whereby a condensed beam of indirect germicidal ultraviolet radiation is projected at said optimal range onto the target area on the patient's body without substantial emanation of ultraviolet radiation outside thereof.

\* \* \* \* \*